United States Patent [19]

Lovelock

[11] 4,260,884
[45] Apr. 7, 1981

[54] CORONA DISCHARGE DEVICES

[75] Inventor: James E. Lovelock, Launceston, England

[73] Assignee: Hewlett-Packard Company, Palo Alto, Calif.

[21] Appl. No.: 885,749

[22] Filed: Mar. 13, 1978

[30] Foreign Application Priority Data

Mar. 11, 1977 [GB] United Kingdom ............... 10332/77

[51] Int. Cl.² ........................ H01T 19/04; G01T 1/185
[52] U.S. Cl. .................................. 250/324; 250/382; 422/98; 422/89
[58] Field of Search ............... 250/324, 426, 374, 423, 250/382, 325, 326; 23/232 E; 422/98, 89; 361/230; 73/23.1

[56] References Cited

U.S. PATENT DOCUMENTS

| 2,604,870 | 7/1952 | Blood et al. | 250/326 |
|---|---|---|---|
| 2,856,533 | 10/1958 | Rosenthal | 250/325 |
| 3,322,500 | 5/1967 | Sternberg | 422/89 |
| 3,464,207 | 9/1969 | Okress | 313/54 |
| 3,668,383 | 6/1972 | Carroll | 250/287 |
| 3,713,773 | 1/1973 | Fontijn et al. | 23/232 E |
| 3,729,672 | 4/1973 | Rosenthal et al. | 250/326 |
| 3,749,929 | 7/1973 | Wooton et al. | 250/361 C |
| 3,832,554 | 8/1974 | Topley | 250/423 |

FOREIGN PATENT DOCUMENTS

| 1042409 | 9/1966 | United Kingdom | 23/232 E |
| 1076564 | 7/1967 | United Kingdom | 361/230 |

Primary Examiner—Alfred E. Smith
Assistant Examiner—Carolyn E. Fields
Attorney, Agent, or Firm—Donald N. Timbie

[57] ABSTRACT

A corona discharge device capable of use as an ionization detector or as a solute switch. Corona discharge pulses of short duration, preferably not exceeding one microsecond, can ionize a gas flow through the device. In the detector mode, electrons produced by the corona discharge can react with a compound to be detected in the gas flow. In the switching mode, the device converts a compound in the gas flow into a reaction product, and fluctuations in output signal of a detector connected to receive flow from the device correspond to the switching frequency of the device and are indicative of the compound in the gas flow.

9 Claims, 7 Drawing Figures

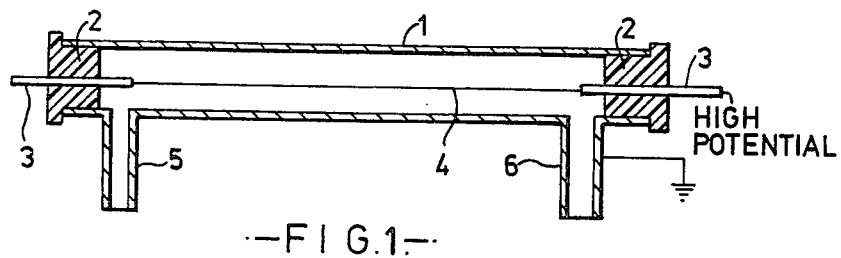
—FIG.1—
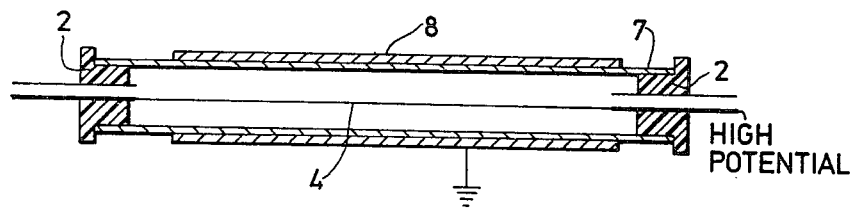
—FIG.2—
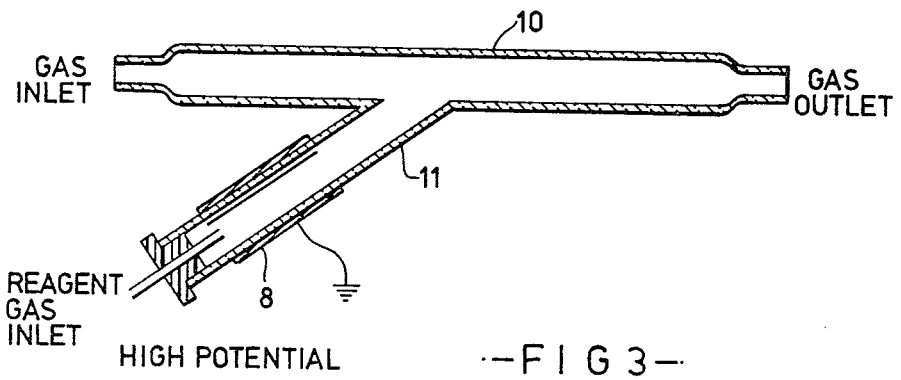
—FIG 3—

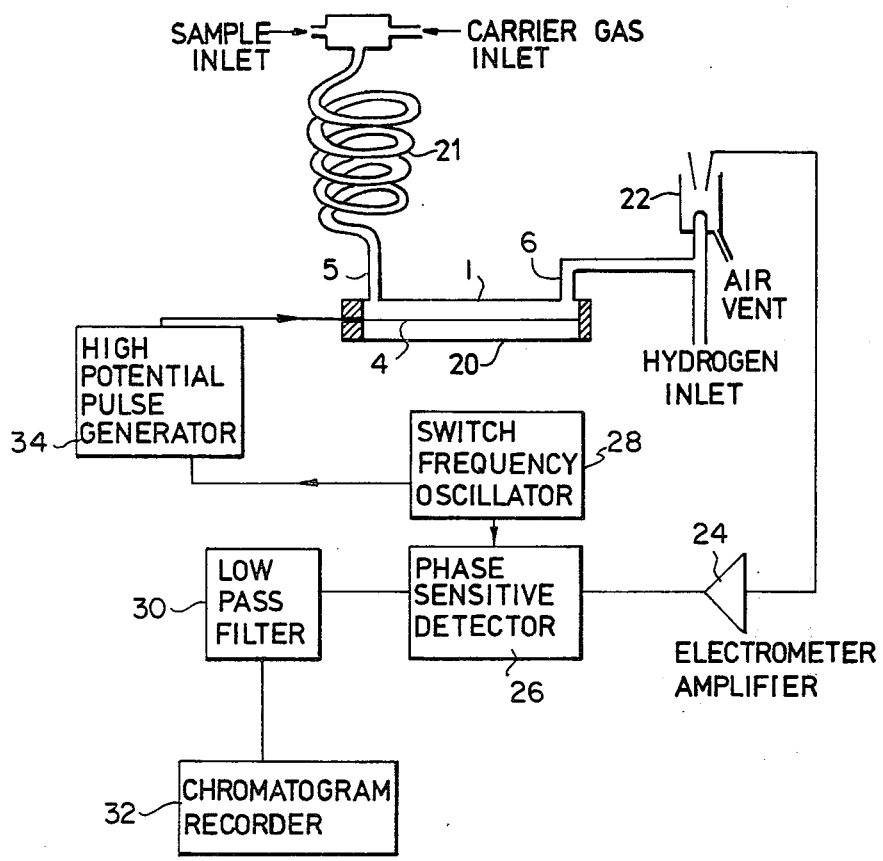
—FIG.4.—

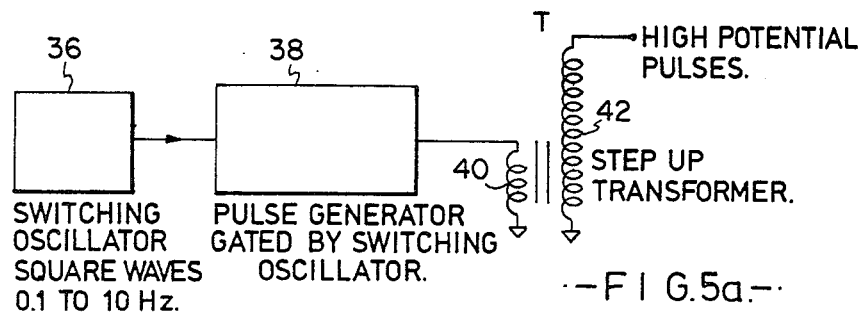
—FIG.5a.—
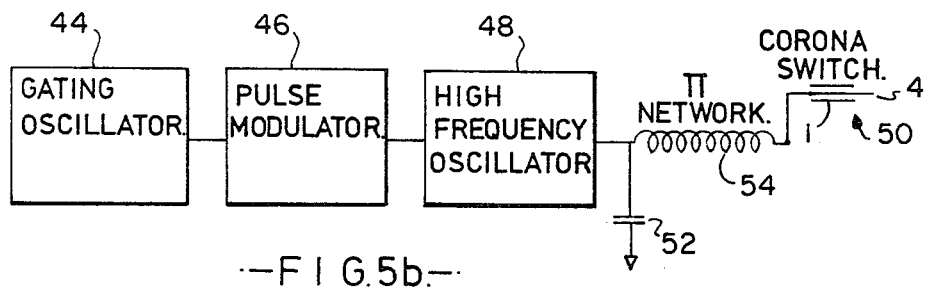
—FIG.5b.—
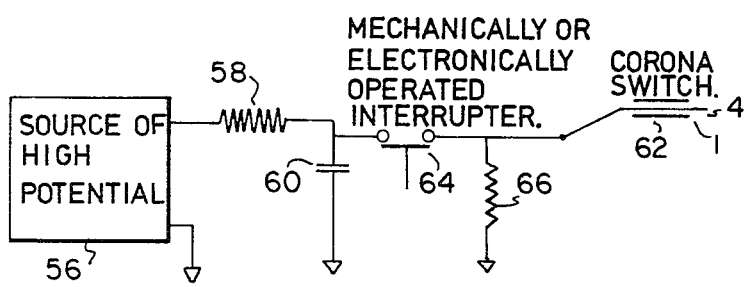
—FIG.5c.—

CORONA DISCHARGE DEVICES

The present invention concerns corona discharge devices and to the use of such devices as analytical tools in gas chromatography and other applications.

Known gas ionisation detectors, such as the electron capture detector, argon and helium ionisation detectors employ a radio-active source of ionising radiation to ionise an atmosphere within the chamber of the detector. For example, in the electron capture detector, the ionising radiation ionises the atmosphere in the detector chamber to produce electrons which, on applying a potential across the electrodes of the detector, give rise to a detector standing current. The introduction of an electro-negative substance into the atmosphere within the chamber, that is a substance capable of capturing or absorbing electrons, results in a reduction in the standing current to provide a distinguishable signal representative of the substance.

A disadvantage of ionisation detectors employing a source of radio-active material is that they have to meet strict health and safety conditions which are enforced to protect operating personnel.

An aim of the present invention is to provide a device capable of generating electrons, ions and activated molecular and atomic species without utilising a radioactive source of ionising radiation.

According to the invention this aim is achieved by utilizing a corona discharge to provide the ionising radiation and preferably the corona discharge occurs at ambient pressure.

It is known that electrical discharges in gases produce a wide range of reactive particles, such as electrons, but it is difficult, if not impossible, to operate smooth low intensity discharges at ambient pressures. At such pressures the discharges tend to be in the form of sparks, arcs or noisy corona discharges. However, this problem can be overcome by supplying to a fine conductor or a discharge point brief pulses of high potential (voltage) or, alternatively, brief packets of high frequency, high potential (voltage) pulses. It has been found that this results in the production of low intensity corona discharges. The pulses can be repeated at regular intervals, for example, in the range 1–100,000 per second to result in a smooth control of the intensity of ionisation.

The electric field applied to the device to produce a corona discharge must be switched off before the electrons or ions produced by the discharge are collected at the electrodes and hence prevented from reacting in the device. For this reason a DC or low frequency corona discharge is not suitable. A field sufficient to initiate a corona discharge will also rapidly scavenge electrons and ions already present in the device. Accordingly, the pulses should be not greater than 1 microsecond in duration and optimally can be 200 nanoseconds. There is reason to assume that even shorter pulses, for example pulses in the region of 1 nanosecond, would be effective but such short pulses might be difficult to achieve with simple and inexpensive equipment.

Pulses of short duration serve two purposes. First, the pulses ionise the gas to release free electrons or to emit electrons from the negative electrode by field emission, or both. Second, it is required that the electrons so produced remain available to react with the component in the gas to be detected or switched in the manner hereinafter described. Pulses of longer duration could scavenge most of the electrons before the electrons could react in the chamber, that is to drive the electrons so rapidly across the ionisation chamber that molecular encounters are rare during the pulse and few electrons remain after the pulse to react with the molecules. It is required to have at least one ion or electron present in the atmosphere within the device to start the corona discharge. This can be provided by cosmic rays, natural radio-activity and other causes but, alternatively, a very weak radio-active source can be included within the device for the purpose of ensuring that at least one ion or electron is present to initiate the discharge. The amount of radioactive material required for this purpose is so small that it will not constitute a hazard and can be measured in micro-curies as opposed to milli-curies present in existing ionisation detectors. The inclusion of such a weak radioactive source is not essential but can result in improved performance of the device.

The invention will be described, by way of example, with reference to the accompanying diagrammatic drawings, in which:

FIGS. 1 to 3 show examples of different forms of corona discharge devices;

FIG. 4 shows an application of such a device;

FIGS. 5a, 5b, and 5c are examples of circuits for prodducing pulses of high potential.

A corona discharge device of FIG. 1 comprises a cylindrical metal tube 1, the ends of the tube being closed by plugs 2 of electrically insulating material, for example PTFE. The plugs 2 carry conductors 3 which support a fine wire 4, for example 50 SWG, which extends coaxially along the length of the tube.

Inlet and outlet ports 5 and 6 respectively are located at opposite ends of the tube 1.

In use, pulses of high potential are applied to the wire, the tube itself being at ground or earth potential. A gas stream is passed through the tube and the corona discharge ionises the gas within the tube.

In FIG. 2, a tube 7 is formed from an electrically insulating material such as glass and is surrounded by a cylindrical metal sheath 8. The gas inlet and outlet ports are supported in the end plugs 2 and the fine wire 4 is attached to and extends between the ports. Such an arrangement could also be used in FIG. 1 or alternatively the FIG. 1 arrangement could be used in FIG. 2. The cylindrical metal sheath is maintained at ground potential while rapid pulses of high potential are applied to the fine wire. A capacitative coupling results between the wire and the metal sheath.

FIG. 3 shows a main tube 10 and a branch tube 11. The main tube and branch tube can be glass and a gas stream flows along the main tube 10. The branch tube 11 comprises a corona discharge device such as shown in FIG. 2. In FIG. 3, a different gas supply is introduced into the branch tube 11 and this supply is chosen to produce specific active particles capable of reacting with the gas flowing along the main tube.

The devices of FIGS. 1 to 3 can function in the manner of ionisation detectors employing radioactive sources. For example, if the corona discharge produces free electrons in the gas within the device and an electron absorber is then introduced into the gas stream, this will result in a detectable difference signal from the device. However, the device can also be used as a switch in conjunction with a standard form of detector. The device can periodically interrupt, convert or destroy the composition of a gas flowing therethrough by reaction with the products produced by corona discharge. Consequently, if the effluent flow from the device is passed into an appropriate detector, the detector will produce an alternating signal output peculiar to the composition being periodically destroyed or converted in the corona discharge device.

FIG. 4 illustrates, diagrammatically, a corona discharge device 20 functioning as a switch and arranged between a chromatographic column 21 and a detector 22, in this case a flame ionisation detector. A sample gas is introduced into the column and is carried through the corona discharge device 20 and into the detector by a carrier gas, for example argon. If the device 20 can produce electrons by corona discharge and if the sample gas is or contains an electron absorber, the sample gas can be detected upon rapid periodic switching of the device on and off as a result of a corresponding alternating signal change at the detector. With this arrangement, electron capturing substances are detected by their specific destruction through reaction with electrons during switching and their presence recorded after synchronous demodulation of the flame ionisation detector signal. Thus, analysis by electron capture can be carried out without the use of a radioactive source and takes advantage of the wide linear dynamic range of the flame ionisation detector.

An electrometer amplifier 24 is connected between the output electrode of the detector 22 and one input of a phase sensitive detector 26, and an output of a switch frequency oscillator 28 is connected to the other input of the detector 26. The output of the detector 26 is coupled via a low pass filter 30 to a chromatogram recorder 32. An output of the switch frequency oscillator 28 is applied to control a high potential pulse generator 34, the output of which is applied to the coaxial wire 4.

In functioning as a switch the corona discharge device alternatively destroys or converts a detectable compound entering into the device into a reaction product which does not produce a signal in the following detector. The detector output accordingly fluctuates in accordance with the switching of the device and the fluctuations are synchronised with the switching of the device to identify the compound. Alternatively, the reverse process can take place. The compound of interest might be such as not to normally produce a response in the detector but, on reaction in the switching device, it can be converted into a detectable product.

The brief pulses of high potential required for the production of low intensity corona can be obtained by a number of electronic circuits. Examples of possible circuits are shown in FIGS. 5a, 5b and 5c. The optimum frequency is considered to be from 100 kilohertz to 50 megahertz.

In FIG. 5a, a switching oscillator 36 which may supply square waves having a frequency between 0.1 and 10 Hz is coupled so as to control a pulse generator 38, the output of which is applied to the primary winding 40 of a step-up transformer T. One end of the primary winding 40 is connected to ground, as is one end of the secondary winding 42. The high potential pulses for causing corona discharge appear at the other end of the secondary winding 42.

In FIG. 5b, the output of a gating oscillator 44 is applied to a pulse modulator having its output coupled so as to control a high frequency oscillator 48. A network is coupled between the output of the oscillator 48 and a corona switch 50. The network 50 is comprised of an input capacitor 52 connected between the output of the oscillator 48 and ground, a series inductor 54 connected between the output of the oscillator 48 and the wire 4, and the capacitance between the wire 4 and the metal tube 1.

In FIG. 5c, the output of a source 56 of high potential is coupled across a resistor 58 and a capacitor 60 connected in series to ground. The voltage across the capacitor 60 is supplied to a corona switch 62 via an interrupter 64. A resistor 66 is connected between the output of the interrupter and ground.

Examples of gases suitable for use with the switching procedure are helium, nitrogen, argon and mixtures of these gases with other gases including hydrogen, oxygen, methane, carbon dioxide, carbon tetrafluoride and others. Different active molecular or atomic species are possible by the appropriate choice of gas or gas mixture.

It is possible to activate a carrier gas, which is otherwise inert, so that it reacts with a compound to be switched. Nitrous oxide for example does not react with organic compounds at temperatures commonly used in gas chromatography. When activated by a discharge, products such as oxygen atoms react and destroy the organic compound. Hence the system forms a switch suitable for use with a gas chromatography detector, such as a flame ionisation or a thermal conductivity detector.

The following table gives examples of reactions.

| Diluent or Carrier Gas | Reagent Gas | Reactive species | Products capable of being switched |
|---|---|---|---|
| Argon, Helium, Nitrogen, Argon/Methane mixture | None | free electrons | electron absorbers, e.g. halogens, halogenated organic compounds, nitro-compounds. |
| Argon, Helium | Argon, Helium | Argon & Helium | All products with ionisation potentials less than the energy of the argon of helium metastable. |
| Argon, Helium, Nitrogen or no carrier gas | oxygen, air nitrous oxide, carbon dioxide | atomic oxygen ozone | Most organic compounds and some oxidisable gases e.g. $NH_3$, $H_2S$, $SO_2$ |
| Argon, Helium, Nitrogen or no carrier gas | Hydrogen Ammonia | Hydrogen atoms | Reducable gases e.g. CO, NO, $CO_2$ |
| Argon, Helium, Nitrogen, or no carrier gas | $CF_4$ $SF_6$ | fluorine atoms | All organic compounds and some oxidisable gases |

In addition to its application as a switching device in conjunction with a detector, the corona discharge device can be used as an electron source for ionisation detectors such as the electron capture, and the argon and helium ionization detectors. The corona discharge device can also serve as an ion source for ionisation smoke and fire detectors. In such applications it does away with the use of radio-active sources hitherto required for the production of electrons or ions.

The rate of production of ions, electrons and other activated species can be controlled over a wide range by varying the frequency of the pulses of potential. This is an inherent convenience so that an optimum can be set for any analytical or other need. A closed loop control system is possible wherein the ion or electron production is sensed by the DC ion current or by the emission of radiation in the range infra red to ultra violet from the discharge. This signal can then be used to control the frequency or the potential of the pulses, preferably the frequency, so that a chosen constant ion production is maintained.

The frequency of the pulses can also be controlled by the signal from the detector connected in the effluent gas stream from the corona discharge device. In this way the frequency and hence the ionization intensity required to completely or partially delete a compound is available.

What is claimed is:

1. A corona discharge device comprising an ionisation chamber having associated electrodes and inlet and outlet means for passage of a gas flow through the chamber, means for establishing corona discharge current pulses between said electrodes in said chamber to effect ionisation within the chamber, said pulses having a duration less than one microsecond.

2. A device according to claim 1 comprising an elongate ionisation chamber having gas inlet and outlet ports at opposite ends thereof, a first electrode being formed at the wall of the chamber and maintained at ground potential, a second electrode being formed by a coaxial wire extending the length of the chamber and electrically insulated from the first electrode.

3. A device according to claim 2 in which the wall of the tube is an electrical insulator and the first electrode is formed about the exterior of the wall to effect a capacitative coupling with the second electrode.

4. A device according to claim 2 in which the outlet from the chamber communicates with a further chamber, said further chamber having inlet and outlet means at the ends thereof for the passage of a gas flow different to the gas flow in the first mentioned chamber.

5. A solute switching system comprising a solute switch for modulating solute concentration in a gas flow and a detector for receiving gas flow from the switch, the switch comprising a corona discharge device operable at ambient pressure and at a variable switching frequency to give low intensity corona discharge pulses which produce reactive species to react with solute flowing through the device, the resulting fluctuations in the solute concentration entering the detector producing corresponding fluctuations in detector output signal and which are indicative of the presence of the solute in the gas flow.

6. A switching system according to claim 5 including means for correlating said fluctuations in detector output signal with the switching frequency of the corona discharge device.

7. A solute switching system comprising
a corona discharge device having an inlet port and an outlet port and means for forming low intensity discharge pulses therein at ambient pressure so as to produce fluctuation in the reactive species to react with solute flowing through the device, the pulses being of such short duration that electrons and ions produced thereby remain in the solute, and
means including detecting means coupled to the outlet of said discharge device.

8. A solute switching system as set forth in claim 7 wherein means are provided for detecting any fluctuation in the solute concentration entering the detector.

9. A solute switching system comprising
a chamber,
electrodes mounted in said chamber,
means defining inlet and outlet ports in said chamber such that gas introduced at the inlet port passes by the electrodes and out of the outlet port,
an ionization detector coupled to receive gas emerging from the outlet port of said chamber, said ionization detector producing an electrical signal at its output that is indicative of the composition of gas flowing into it from the outlet port of said chamber,
means for applying pulses of voltage between said electrodes so as to produce corona discharge therebetween,
a phase sensitive detector having two inputs and an output, means for applying electrical signals to one input of said phase sensitive detector that are synchronized with the pulses applied to said electrodes, and
means for applying the electrical signals at the output of said ionization chamber to the other input of said phase sensitive detector.

* * * * *

UNITED STATES PATENT AND TRADEMARK OFFICE
CERTIFICATE OF CORRECTION

PATENT NO. : 4,260,884
DATED : April 7, 1981
INVENTOR(S) : James E. Lovelock

It is certified that error appears in the above-identified patent and that said Letters Patent are hereby corrected as shown below:

Column 2    line 25    "prodducing" should read -- producing --

Column 4    line 17    "reaches" should read -- reacts --

Signed and Sealed this

Fourth Day of August 1981

[SEAL]

Attest:

GERALD J. MOSSINGHOFF

Attesting Officer    Commissioner of Patents and Trademarks